United States Patent [19]

Tsao

[11] 4,071,571
[45] Jan. 31, 1978

[54] CONTROL OF MOLTEN SALT OXIDATION IN PRODUCTION OF CHLORINATED HYDROCARBONS

[75] Inventor: Utah Tsao, Jersey City, N.J.

[73] Assignee: The Lummus Company, Bloomfield, N.J.

[21] Appl. No.: 660,251

[22] Filed: Feb. 23, 1976

[51] Int. Cl.² ............................................. C07C 21/00
[52] U.S. Cl. ...................... 260/654 R; 260/654 A; 260/650 R; 260/656 R; 260/659 R; 260/659 A; 260/660; 260/662 A; 260/662 R
[58] Field of Search ............... 260/660, 654 R, 654 A, 260/659 R, 659 A, DIG. 42, 662 A, 656 R; 208/DIG. 1

[56] References Cited

U.S. PATENT DOCUMENTS

| | | | |
|---|---|---|---|
| 2,752,402 | 6/1956 | Pye | 260/659 A |
| 3,427,359 | 2/1969 | Rectenwald et al. | 260/659 A |
| 3,709,951 | 1/1973 | Hutson et al. | 208/DIG. 1 |
| 3,857,794 | 12/1974 | Carey | 208/113 |
| 3,865,886 | 2/1975 | Schindler et al. | 260/654 R |
| 3,872,174 | 3/1975 | Bellis | 260/659 R |
| 3,914,328 | 10/1975 | Blake | 260/654 A |

Primary Examiner—Herbert Levine
Assistant Examiner—Joseph A. Boska
Attorney, Agent, or Firm—Marn & Jangarathis

[57] ABSTRACT

In the production of chlorinated hydrocarbons by contacting a molten salt mixture of the higher and lower chloride of a multivalent metal, such as a mixture of cuprous and cupric chloride, with molecular oxygen to effect oxidation to the oxychloride, followed by use of the oxidized salt for the production of chlorinated hydrocarbons, the quantity of carbon dioxide vented from the system is determined, and oxygen introduction is decreased in response to increases in vented carbon dioxide to decrease oxychloride concentration and limit carbon dioxide production.

6 Claims, 1 Drawing Figure

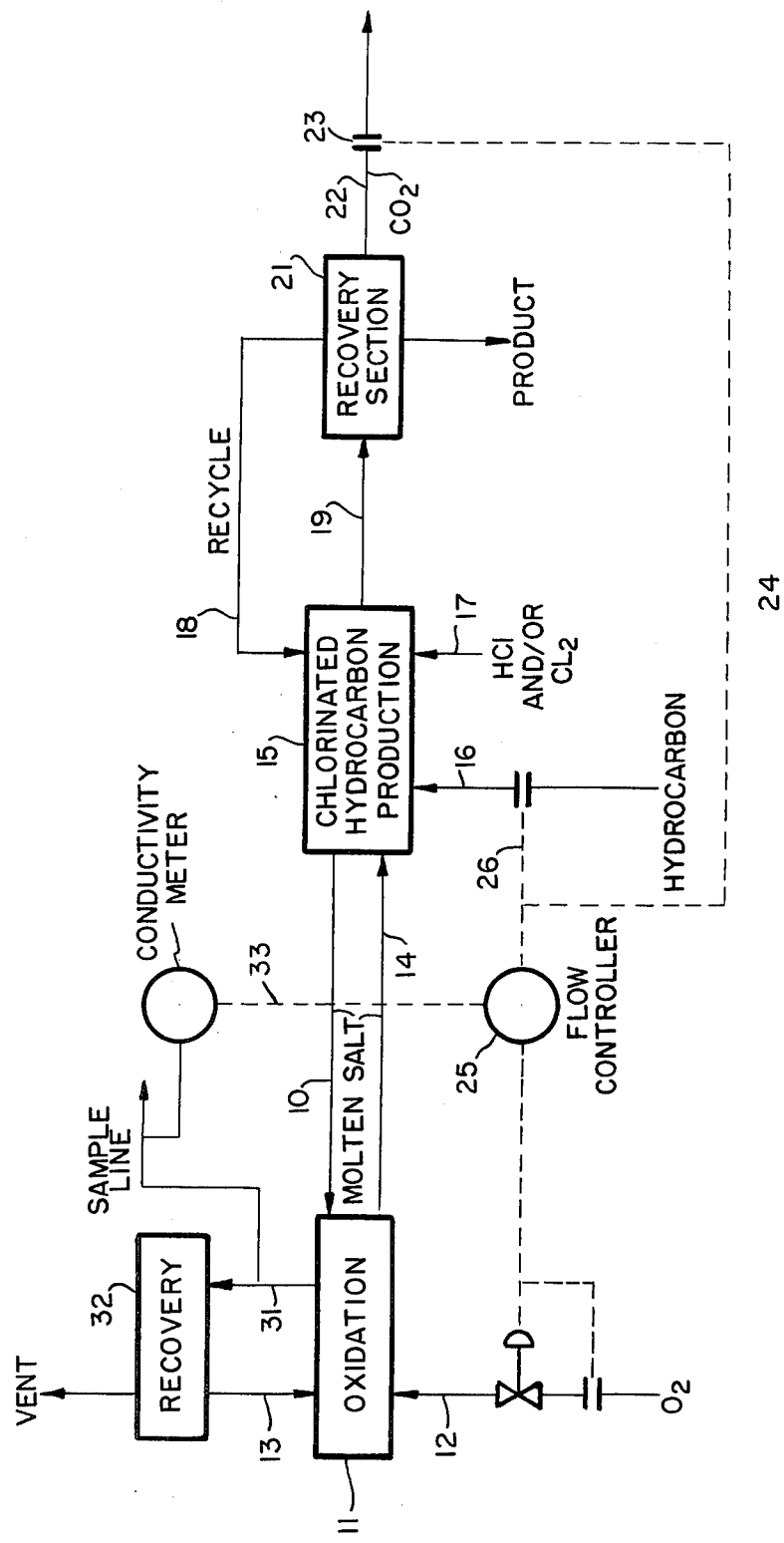

CONTROL OF MOLTEN SALT OXIDATION IN PRODUCTION OF CHLORINATED HYDROCARBONS

This invention relates to the production of chlorinated hydrocarbons, and more particularly, to a new and improved process for producing chlorinated hydrocarbons by the use of molten salts. Still more particularly, the present invention relates to the control of molten salt oxidation in the production of chlorinated hydrocarbons.

In the production of chlorinated hydrocarbons by the use of molten salts, a molten mixture of a multivalent metal chloride in its higher and lower valence state, such as a mixture of cuprous and cupric chloride, is contacted in the first reactor with molecular oxygen to effect oxidation of the salt and produce the corresponding oxychloride. The molten salt, containing oxychloride, is then introduced into a chlorinated hydrocarbon production zone wherein the molten salt is contacted with a hydrocarbon, resulting in production of a chlorinated hydrocarbon. The effluent withdrawn from the chlorinated hydrocarbon production zone includes carbon dioxide, and such carbon dioxide production represents a loss of hydrocarbon feed.

Applicant has found that carbon dioxide production in the chlorinated hydrocarbon production zone is related to the amount of oxygen transferred to the chlorinated hydrocarbon production zone by the molten salt, with an increase in the oxychloride content of the molten salt resulting in increased carbon dioxide production. As a result, excess carbon dioxide production can be prevented by controlling the oxychloride content of the molten salt; however, there is no easy and quick way of determining the oxychloride content of the molten salt.

Accordingly, there is a need for a process for controlling carbon dioxide production by controlling the oxychloride content of of the molten salt.

An object of the present invention is to provide for production of chlorinated hydrocarbons by the use of molten salts.

Another object of the present invention is to provide for control of carbon dioxide production in the production of chlorinated hydrocarbons by the use of molten salts.

A further object of the present invention is to control carbon dioxide production by controlling the oxychloride content of the molten salt.

These and other objects of the present invention should be more readily apparent from reading the following description thereof.

In accordance with the present invention, there is provided a process for producing a chlorinated hydrocarbon by contacting a molten salt containing the higher and lower valent chlorides of a multivalent metal with molecular oxygen to produce the oxychloride of the multivalent metal, with the oxidized molten salt then being contacted in a chlorinated hydrocarbon production zone with a hydrocarbon to produce an effluent containing chlorinated hydrocarbon and carbon dioxide wherein net carbon dioxide is vented from the chlorinated hydrocarbon production system, with the rate of introduction of oxygen into the system being controlled in response to the quantity of vented carbon dioxide to thereby maintain the quantity of oxychloride present in the molten salt to below a predetermined amount and thereby limit carbon dioxide production.

More particularly, in order to prevent a build-up of carbon dioxide in the system, carbon dioxide is vented therefrom, and Applicant has found that the amount of carbon dioxide produced in the chlorinated hydrocarbon production reactor can be controlled to below a predetermined amount by determining the quantity of carbon dioxide vented from the system, and reducing the amount of oxygen introduced into the system in response to an increase in the quantity of vented carbon dioxide above a predetermined amount. Thus, Applicant has found that the quantity of carbon dioxide vented from the system is a convenient means of determining the amount of carbon dioxide produced in the chlorinated hydrocarbon production reactor, and that such production can be limited by controlling the amount of oxygen introduced into the system in response to the quantity of carbon dioxide vented from the system. The amount of oxygen introduced into the system can be controlled in direct response to the quantity of carbon dioxide vented, and more preferably, in response to the carbon dioxide vented expressed as a ratio of vented carbon dioxide to net hydrocarbon feed. In accordance with the present invention wherein carbon dioxide production in the chlorinated hydrocarbon production reactor is controlled by determining the amount of vented carbon dioxide, carbon dioxide production can be controlled, without the necessity of providing difficult controls for detecting either the amount of carbon dioxide present in the effluent withdrawn from the chlorinated hydrocarbon production reactor or the amount of oxychloride present in the molten salt introduced into the chlorinated hydrocarbon production reactor. The quantity of carbon dioxide production which is acceptable in the production of chlorinated hydrocarbons will vary with the system and production requirements, and the determination of such acceptable quantities is within the scope of those skilled in the art from the present teachings. The present invention is particularly directed to providing means for limiting such carbon dioxide production to predetermined acceptable limits.

The salt mixture contains the higher and lower valent chlorides of a multivalent metal, with such multivalent metals generally being either manganese, iron, copper, cobalt, chromium or mixtures thereof, with the preferred metal chlorides being the copper chlorides. In employing the salt mixture in molten form, the salt mixture generally also includes a metal salt melting point depressant which is non-volatile and resistant to the oxygen, at the process conditions, in order to maintain the multivalent metal chloride in the form of a melt. The melting point depressant is generally either an alkali metal chloride or a heavy metal chloride; i.e., heavier than copper, of Groups I, II, III and IV of the Periodic Table. The preferred melting point depressant is potassium chloride. A preferred molten salt mixture contains from about 20 to about 40%, by weight, potassium chloride, with the remainder being copper chlorides.

The hydrocarbon feed may be any one of a wide variety of hydrocarbons, including, aliphatic hydrocarbons, including both saturated and mono-olefinically unsaturated hydrocarbons, preferably having from 1 to 4 carbon atoms, or aromatic hydrocarbons; in particular, benzene. The preferred feeds are either ethane and- /or ethylene to produce $C_2$ chlorinated hydrocarbons or methane to produce chloromethanes.

In accordance with a further feature of the present invention, there is provided a means for insuring that a predetermined minimum quantity of oxychloride is present in the molten salt introduced into the chlorinated hydrocarbon production zone. More particularly, in oxidizing the molten salt to produce the oxychloride of the multivalent metal, a gaseous effluent is withdrawn from the oxidation reaction zone, and such gaseous effluent contains, in addition to other components, water vapor and equilibrium amounts of hydrogen chloride. Applicant has found that the amount of hydrogen chloride present in the effluent is increased, and the amount of water vapor present in the effluent is decreased, in response to decreases in the amount of oxychloride present in the molten salt withdrawn from the oxidation reaction zone. As a result, in accordance with a further feature of the present invention, the amount of hydrogen chloride present in the gaseous effluent withdrawn from the oxidation reaction zone is determined, with an increase in the hydrogen chloride content being indicative of a decrease in the amount of oxychloride present in the molten salt. In accordance with this feature of the present invention, the amount of oxygen introduced into the oxidation reaction zone is controlled, at the minimum, in response to a recovered aqueous hydrogen chloride concentration which exceeds a predetermined maximum amount. In this manner, an increase in the hydrogen chloride concentration above a predetermined maximum amount is representative of a decrease in the oxychloride concentration of the molten salt below a predetermined minimum amount, and in response to such increase in concentration of hydrogen chloride, the amount of oxygen introduced into the oxidation reaction zone is increased in order to provide the predetermined minimum oxychloride concentration in the molten salt withdrawn from the oxidation reaction zone.

The hydrogen chloride concentration of the aqueous hydrogen chloride recovered from the gaseous oxidation reaction zone effluent can be determined by any one of a wide variety of procedures, with such concentration preferably being determined by either the conductivity of the hydrogen chloride solution or the density of the hydrogen chloride solution, with a conductivity determination being especially preferred. A conductivity determination is preferred in that the changing conductivity of the aqueous hydrogen chloride solution is more sensitive to hydrogen chloride concentration than density. Furthermore, conductivity meters are more accurate than density meters. The instrumentation employed for determining the conductivity and/or density of an aqueous hydrogen chloride solution are well known in the art, and no details with respect to such instrumentation and/or the manner in which such instrumentation can be employed to prevent the quantity of oxygen introduced into the oxidation zone from dropping below a predetermined minimum, is deemed necessary for a complete understanding of the present invention.

Thus, in accordance with the further feature of the present invention, the amount of oxygen introduced into the oxidation reaction zone is controlled, in response to both the aqueous hydrogen chloride concentration of the oxidation reaction effluent, and the quantity of carbon dioxide vented from the system. The amount of oxygen introduced into the system is controlled in response to both the aqueous hydrogen chloride concentration of the oxidation reactor effluent and the vented carbon dioxide in that Applicant discovered that aqueous hydrogen chloride concentration is sensitive to small changes in the oxychloride concentration at the lower oxychloride concentrations, whereas the quantity of carbon dioxide vented from the system is sensitive to small changes in oxychloride concentrations at higher oxychloride concentrations.

The invention will be further described with respect to an embodiment thereof illustrated in the accompanying drawing wherein:

The drawing is a simplified schematic flow diagram of an embodiment of the present invention.

Referring now to the drawing, a molten mixture of a multivalent metal chloride in its higher and lower valence state, such as a mixture of cuprous and cupric chloride, further containing a melting point depressant, such as potassium chloride, in line 10, is introduced into an oxidation reaction zone, schematically indicated as 11, wherein the molten salt is contacted with molecular oxygen (for example as air) introduced through line 12 to effect oxidation thereof, by production of the oxychloride. In addition, aqueous hydrogen chloride in line 13, obtained as hereinafter described, is introduced into the oxidation reaction zone wherein the chloride values thereof are recovered by generation of a higher valent metal chloride; i.e., cupric chloride. The oxidation reaction zone 11 is generally operated at a temperature from about 600° to about 900° F and at a pressure of from about 1 to about 20 atmospheres. A gaseous stream (not shown) containing chlorine values in the form of hydrogen chloride and/or chlorine, produced from combustion of waste chlorinated hydrocarbon by-products may also be introduced into the oxidation reaction zone 11 in order to recover the chlorine values thereof by generation of the higher valent metal chloride.

A molten salt mixture, containing cuprous chloride, cupric chloride, and copper oxychloride, and the melting point depressant, is withdrawn from oxidation reaction zone 11 through line 14 and introduced into a chlorinated hydrocarbon production zone, schematically indicated as 15, wherein the molten salt is contacted with a hydrocarbon feed, introduced through line 16, hydrogen chloride and/or chlorine, introduced through line 17, and a recycle stream, introduced through line 18. The recycle stream in line 18 generally contains unreacted hydrocarbon, as well as chlorinated hydrocarbon intermediates to be converted to the desired chlorinated hydrocarbon product. The chlorinated hydrocarbon production zone 15 is generally operated at temperatures in the order of from about 700° to about 1200° F and at pressures from about 1 to about 20 atmospheres.

A chlorinated hydrocarbon production effluent is withdrawn from chlorinated hydrocarbon production zone 15 through line 19, and such effluent includes, unreacted hydrocarbon, chlorinated hydrocarbon, inerts, such as nitrogen and carbon monoxide, carbon dioxide, water vapor and hydrogen chloride. The effluent in line 19 is introduced into a recovery section, schematically indicated as 21, wherein the effluent is subjected to different recovery operations to effect recovery of chlorinated hydrocarbon product, a recycle stream and carbon dioxide to be vented from the system. The particular details for recovering the various components form no part of the present invention and, accordingly, no further description in this respect is deemed necessary for a full understanding of the invention.

As known in the art, in order to prevent a build-up of carbon dioxide in the chlorinated hydrocarbon production system, the recovery section 21 includes means for separating carbon dioxide from the reaction effluent for venting from the system. Thus, for example, all or a portion of the effluent may be subjected to an operation for separately recovering carbon dioxide therefrom, with such carbon dioxide being eventually vented from the system. In accordance with a well known procedure, all or a portion of the effluent stream is contacted with an acid gas absorption solution in an acid gas absorption tower, which results in selective absorption of carbon dioxide from the gas stream. The carbon dioxide rich absorption solution is then introduced into a stripper wherein carbon dioxide is stripped from the absorption solution for venting from the system. The lean absorption solution recovered from the stripper is then introduced into the absorption tower to effect recovery of carbon dioxide. The carbon dioxide absorption solutions are well known in the art, and as representative examples of such absorption solutions, there may be mentioned: amine absorption solutions, including alcohol amines; carbonates, including organic and inorganic carbonates; sulfolanes, dioxolanes, etc. In view of the fact that procedures for separating carbon dioxide from a gaseous effluent are well known in the art, no further details in this respect are deemed necessary for a full understanding of the invention.

As a result of the carbon dioxide separation operation in recovery section 21, a gas stream comprised of essentially only carbon dioxide is withdrawn from the recovery section 21 through line 22. The line 22 is provided with a suitable flow measuring instrument, schematically indicated as 23, which measures the quantity of carbon dioxide vented from the system and provides a signal through line 24 to a flow controller 25 representative of the quantity of carbon dioxide vented from the chlorinated hydrocarbon production system through line 22. In accordance with the illustrated embodiment, the flow controller 25 is also provided with a signal through line 26 representative of the quantity of hydrocarbon introduced as net feed through line 16. The flow controller 25 operates in accordance with a signal representative of the ratio of the quantity of carbon dioxide vented through line 22 to the quantity of hydrocarbon introduced as feed through line 16.

As hereinabove noted, when the ratio of carbon dioxide vented through line 22 to the hydrocarbon feed introduced through line 16 increases to above a predetermined amount, the flow controller 25 operates to decrease the quantity of oxygen introduced into the oxidation reaction zone 11 through line 12. Such reduction in oxygen feed results in a reduction in the oxychloride content of the molten salt withdrawn through line 14, which also results in a reduction in the quantity of carbon dioxide produced in the chlorinated hydrocarbon production zone 15. In this manner, the amount of carbon dioxide generated in the chlorinated hydrocarbon production zone 15 is limited to below a predetermined amount. It is also to be understood that the flow controller 25 could also be operated in response to only the quantity of carbon dioxide vented through line 22 instead of the ratio of this quantity to the quantity of hydrocarbon introduced through line 16.

As hereinabove noted, the chlorinated hydrocarbon production system may also be provided with means for ensuring a minimum quantity of oxychloride in the molten salt. In accordance with this feature of the present invention, a gaseous effluent withdrawn from oxidation reaction zone 11 through line 31 contains water vapor, hydrogen chloride, any nitrogen introduced with the oxygen containing gas and any carbon oxide(s) introduced with a combustion effluent resulting from the burning of chlorinated hydrocarbon by-products. The gas in line 31 is introduced into a recovery zone 32 wherein aqueous hydrogen chloride is separated from the gaseous effluent. Such separation of aqueous hydrogen chloride may be easily effected by condensation of the aqueous hydrogen chloride by either indirect cooling or direct quench cooling. The aqueous hydrogen chloride recovered from the gaseous effluent in recovery section 32 is recycled to the oxidation reaction zone 11 through line 13 in order to recover the chlorine values thereof. In accordance with this feature of the invention, the hydrogen chloride concentration may be easily determined by condensing aqueous hydrogen chloride from a sample portion of the effluent in line 31 and determining the hydrogen chloride concentration thereof; e.g., by a conductivity meter, and such conductivity meter provides a signal to flow controller 25 through line 33 representative of such hydrogen chloride concentration. An increase in the hydrogen chloride concentration in line 31 above a predetermined amount indicates that oxychloride content of the melt has fallen below a desired amount and at such point the flow controller 25 operates to increase the quantity of molecular oxygen introduced into the oxidation reaction zone 11 through line 12 in order to insure that there is a minimum quantity of molecular oxygen provided to the chlorinated hydrocarbon production zone as oxychloride.

Thus, in accordance with the preferred feature of the present invention, the quantity of oxygen introduced into the chlorinated hydrocarbon production zone, as oxychloride, is limited in response to the carbon dioxide vented from the overall system, to limit carbon dioxide production, and the quantity of molecular oxygen introduced into the chlorinated hydrocarbon production zone, as oxychloride, is prevented from falling below a predetermined amount in response to the quantity of hydrogen chloride withdrawn from the oxidation reaction zone, as conveniently determined by aqueous hydrogen chloride concentrations.

It is to be understood that within the spirit and scope of the present invention the invention may be practiced other than as hereinabove described with respect to the preferred embodiment. Thus, for example, in some cases, carbon dioxide may be purged from the system along with unreacted hydrocarbon in a purge stream, essentially free of chlorinated hydrocarbon. In such an embodiment, the quantity of carbon dioxide vented from the system is determined by a carbon dioxide analyzer, rather than with a flow meter as described with respect to the embodiment wherein only carbon dioxide is vented.

The present invention is particularly advantageous in that it permits control of carbon dioxide production in the chlorinated hydrocarbon production zone without the necessity of determining the amount of carbon dioxide in the effluent withdrawn from the chlorinated hydrocarbon production zone or the amount of oxygen introduced into the chlorinated hydrocarbon production zone in the molten salt.

Numerous modification and variations of the present invention are possible in light of the above teachings, and, therefore, within the scope of the appended claims, the invention may be practiced otherwise than as particularly described.

What is claimed is:

1. In a process for producing a chlorinated hydrocarbon in a chlorinated hydrocarbon production system by contacting in a first reaction zone a molten salt containing the higher and lower valent chlorides of a multivalent metal with molecular oxygen to produce the oxychloride of the multivalent metal, contacting in a second reaction zone the salt containing the oxychloride with a hydrocarbon to produce an effluent containing chlorinated hydrocarbon and carbon dioxide and venting a carbon dioxide containing stream from the chlorinated hydrocarbon production system, the improvement comprising:

decreasing the amount of oxygen employed in producing the oxychloride in the first reaction zone in response to an increase in the quantity of carbon dioxide in the vented carbon dioxide containing stream to decrease the quantity of oxychloride present in the molten salt and maintain the quantity of oxychloride present in the molten salt to below a predetermined amount and thereby limit carbon dioxide production.

2. The process of claim 1 wherein the oxygen introduction is controlled in response to the ratio of vented carbon dioxide to net hydrocarbon feed.

3. The process of claim 1 wherein the carbon dioxide is vented in a separate stream and the quantity of vented carbon dioxide is determined by measuring the flow rate of said separate stream.

4. The process of claim 1 wherein an effluent withdrawn from the first reaction zone includes hydrogen chloride; and further comprising:

maintaining a minimum quantity of oxychloride in the molten salt by increasing the quantity of oxygen employed in producing the oxychloride in response to an increase in the hydrogen chloride present in the effluent withdrawn from the first reaction zone to thereby increase the oxychloride content of the molten salt.

5. The process of claim 4 wherein the hydrogen chloride present is determined by recovering aqueous hydrogen chloride and determining the hydrogen chloride concentration thereof, with the quantity of oxygen employed being increased in response to an increase in hydrogen chloride concentration.

6. The process of claim 5 wherein the hydrogen chloride concentration is determined by measuring the conductivity of the aqueous hydrogen chloride.

* * * * *